United States Patent [19]
Danielson et al.

[11] Patent Number: 6,136,338
[45] Date of Patent: Oct. 24, 2000

[54] ORAL VETERINARY COMPOSITION CONTAINING A FLUOROQUINOLONE ANTIBACTERIAL AGENT POSSESSING SUPERIOR ABSORPTION PROPERTIES AND AN EXTENDED DURATION OF THERAPEUTIC ANTIMICROBIAL BLOOD LEVELS, AND A METHOD OF TREATING MICROBIAL INFECTION IN A RUMINANT

[75] Inventors: Douglas W. Danielson, Apple Valley; Eric Nichols; Brent Husband, both of Mendota Heights, all of Minn.

[73] Assignee: American Cyanamid Company, Wayne, N.J.

[21] Appl. No.: 09/158,769

[22] Filed: Sep. 23, 1998

Related U.S. Application Data

[63] Continuation of application No. 08/470,405, Jun. 6, 1995, Pat. No. 6,024,979.

[51] Int. Cl.[7] .............................. A61K 9/08; A61K 9/10; A61K 9/14; A61K 9/20; A61K 9/48
[52] U.S. Cl. .......................... 424/438; 424/442; 424/451; 424/455; 424/464; 424/466; 424/489; 514/937; 514/944
[58] Field of Search .................................... 424/451, 455, 424/464, 489, 466, 438, 442; 514/944, 937

[56] References Cited

U.S. PATENT DOCUMENTS

| | | | |
|---|---|---|---|
| 4,670,444 | 6/1987 | Grohe et al. | 514/300 |
| 5,179,096 | 1/1993 | Gentilini et al. | 514/253 |
| 5,334,589 | 8/1994 | Al-Razzak et al. | 514/185 |
| 5,607,942 | 3/1997 | Petersen et al. | 546/200 |

*Primary Examiner*—James M. Spear
*Attorney, Agent, or Firm*—Oblon, Spivak, McClelland, Maier & Neustadt, P.C.

[57] ABSTRACT

The present invention concerns a formulation for an oral veterinary composition containing a fluoroquinolone antimicrobial agent or a pharmaceutically acceptable salt thereof, and a method of treating a microbial infection in a ruminant. The present veterinary composition, when administered orally to a ruminating animal (e.g., a cow or a feedlot calf), allows the fluoroquinolone to be readily and extensively absorbed from the rumen into the circulating blood and provides an unexpectedly extended duration of therapeutic antimicrobial blood level.

23 Claims, 4 Drawing Sheets

ORAL VETERINARY COMPOSITION CONTAINING A FLUOROQUINOLONE ANTIBACTERIAL AGENT POSSESSING SUPERIOR ABSORPTION PROPERTIES AND AN EXTENDED DURATION OF THERAPEUTIC ANTIMICROBIAL BLOOD LEVELS, AND A METHOD OF TREATING MICROBIAL INFECTION IN A RUMINANT

This application is a continuation of 08/470,405 filed Jun. 6. 1995, U.S. Pat. No. 6,024,979.

BACKGROUND OF THE INVENTION

1. Field of the Invention

The present invention concerns an oral veterinary composition, containing the fluoroquinolone antimicrobial agent difloxacin or a pharmaceutically acceptable salt thereof. When administered orally to a ruminating animal (e.g., a cow or a feedlot calf), the present veterinary composition surprisingly provides (1) ready and extensive absorption of the fluoroquinolone from the rumen into the circulating blood and (2) an unexpectedly extended duration of therapeutic antimicrobial blood level.

2. Discussion of the Background

It is commonly believed that orally administered antimicrobials are not readily absorbed from the gastrointestinal tract of ruminating animals. Typically, the drug will be poorly absorbed, and will show blood levels of questionable therapeutic efficacy. Typically, the blood levels of an orally-administered antimicrobial are substantially lower than that of a dose administered parenterally. It is believed that fluoroquinolones are biodegraded in the rumen of adult ruminating animals, resulting in less active ingredient available for absorption.

The present Inventors have discovered that orally administered difloxacin is well-absorbed into a ruminant's blood and persists over a surprisingly long period of time, and at a level nearly equal the same dose of the drug administered parenterally. These are both unexpected and beneficial effects.

SUMMARY OF THE INVENTION

Accordingly, one object of the present invention is to provide a novel veterinary composition providing a blood concentration of a fluoroquinolone antimicrobial nearly equal to the concentration provided by the same dose of the drug administered parenterally.

A further object of the present invention is to provide a novel veterinary composition which provides an effective concentration of antimicrobial agent in the blood stream of a ruminating or pre-ruminating (including a milk-fed non-ruminating) ruminant over an extended length of time.

A further object of the present invention is to provide a simple and effective method for treating bacterial infections in ruminants.

These and other objects, which will become apparent during the following detailed description of the preferred embodiments are provided by an oral veterinary composition, comprising an effective amount of difloxacin or a pharmacologically acceptable salt thereof, in a pharmacologically acceptable, orally acceptable carrier, and a method of treating bacterial infection in a ruminant, comprising the step of orally administering the present veterinary composition to a ruminant in need thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

The present invention concerns an oral veterinary composition containing a fluoroquinolone (preferably difloxacin) or a pharmaceutically acceptable salt thereof.

In the present invention, a veterinary composition providing an extended duration of therapeutic antimicrobial blood levels is one formulated in a manner which provides an effective concentration of a fluoroquinolone, or pharmacologically acceptable salt thereof, for a length of time sufficiently long to effectively treat a microbial (e.g., bacterial) infection. In a preferred embodiment, the present veterinary composition provides a concentration of the fluoroquinolone (or a pharmacologically acceptable salt thereof) in the ruminant which exceeds the $MIC_{90}$ level for a given bacterium or bacteria for a length of time of at least 24 hours, and more preferably at least 48 hours, thus enabling a daily or less frequent dosing regimen.

The present invention also concerns a method of treating a bacterial infection in a ruminant which may comprise, consist essentially of, or consist of, orally administering an effective amount of the present composition to a ruminant in need thereof.

In the context of the present application, a "non-ruminating" or "pre-ruminating" ruminant is considered to be an animal still nursing or otherwise ingesting little or no roughage (e.g., a "calf" feeding on milk). The rumen is not designed to digest milk, and as a result, the non-ruminating or nursing animal is able to "tunnel" milk directly into its stomach, thus bypassing the rumen. The rumen of a ruminant is induced to function as a result of feeding grasses, roughages or concentrates (e.g., hay, alfalfa, corn, etc.) to the animal. The development of a functioning rumen also depends upon other factors, such as the physiological development of the particular animal. Typically, however, feeding roughages or concentrates to a nursing animal of from 3 to 8 months of age will result in the onset of normal physiological functions of the rumen (i.e., the ability to digest cellulosic materials).

In the present application, the phrase "consisting essentially of" refers to (a) one or more additional components in the composition which do not materially affect the properties of the composition, and/or (b) one or more additional steps in the method which do not materially affect the beneficial effects of the method.

Fluoroquinolone antimicrobial agents, including difloxacin, pharmaceutically acceptable salts thereof, pharmaceutical compositions containing the same and general methods of treating bacterial infections (including infections in non-ruminant animals) are disclosed in U.S. Pat. Nos. 4,730,000 and 5,145,853, the entireties of which are incorporated herein by reference. These antimicrobial agents and salts possess a wide spectrum of antimicrobial activity, including activity against gram-positive and gram-negative microorganisms, such as Staphylococcus, Lactobacillus, Streptococcus, Sarcina, Escherichia, Enterobacter, Klebsiella, Pseudomonas, Acinetobacter, Proteus, Citrobacter, Nisseria, Bacillus, Bacteroides, Peptococcus, Clostridium, Salmonella, Shigella, Serratia, Haemophilus, Pasteurella, Brucella, and others.

Pharmaceutically acceptable salts include, e.g., salts obtained by reacting a fluoroquinolone with a mineral acid such as hydrochloric acid, sulfuric acid, sodium hydrogen sulfate, phosphoric acid, boric acid, nitric acid, etc.; an alkyl- or arylsulfonic acid such as methanesulfonic acid, ethanesulfonic acid, laurylsulfonic acid, benzenesulfonic acid, toluenesulfonic acid, etc.; a carboxylic acid or fatty acid such as acetic acid, propionic acid, valeric acid, oxalic acid, maleic acid, succinic acid, fumaric acid, benzoic acid, tartaric acid, citric acid, lactic acid, oleic acid, palmitic acid, stearic acid, lauric acid, glucoheptonic acid, etc. A "free base equivalent weight" of a pharmaceutically acceptable salt of a fluoroquinolone refers to the corresponding weight of the salt which provides the equivalent weight of free base fluoroquinolone. For example, a composition containing 1.09 g of difloxacin hydrochloride provides a "tree base equivalent weight" of 1.00 g of difloxacin.

The present veterinary composition also comprises a pharmaceutically acceptable, orally acceptable carrier. A carrier is "orally acceptable" if it can be administered to a ruminant orally, and can be digested by the ruminant. Orally acceptable carriers include conventional solid and liquid carriers, excipients and/or diluents which are digestible in ruminants which can be sterilized, if desired or necessary.

Solid dosage forms for oral administration include capsules, tablets, pills, powders, granules, effervescing granules, gels, pastes, troches and pastilles. In such solid dosage forms, the active compound is admixed with at least one conventional inert diluent such as cellulose, silica, sucrose, lactose, starch or modified starch. Such dosage forms can also comprise, as in normal practice, additional substances other than inert diluents, e.g., conventional lubricating agents such as magnesium stearate. In the case of capsules, tablets and pills, the dosage forms may also comprise conventional buffering agents. Tablets and pills can additionally be prepared with conventional enteric coatings.

Liquid dosage forms for oral administration include pharmaceutically acceptable emulsions, solutions, suspensions, syrups and elixirs containing conventional inert diluents, such as water. Besides such inert diluents, the present composition may also include adjuvants, such as wetting agents, emulsifying and suspending agents, and sweetening, flavoring and perfuming agents.

In a preferred embodiment, the present veterinary composition is in the form of a bolus. In the field of veterinary medicine, a "bolus" typically refers to a large pill (e.g. ≧5 grams). In the present application, a "bolus" refers to a solid ready-to-swallow pharmaceutical preparation, which may be administered orally and which may have extended duration of therapeutic antimicrobial blood levels properties.

In a preferred form, the present bolus contains a sufficient amount of fluoroquinolone (more preferably, difloxacin) or a pharmaceutically acceptable salt thereof to provide an effective dosage of the antimicrobial in the ruminant to which the bolus is administered, even if only administered once daily or less frequently to the ruminant. Thus, the present bolus preferably contains at least 100 mg (for example, for administration to a pre-ruminating or non-ruminating ruminant), more preferably at least 1,000 mg (for example, for administration to a ruminating ruminant), and even more preferably at least 1,500 mg of the fluoroquinolone (preferably difloxacin) or a free base equivalent weight of a pharmaceutically acceptable salt thereof. From a practical perspective, however, the present bolus may contain, for example, a maximum of 10,000 mg of difloxacin (preferably at most 5,000 mg) or a free base equivalent weight of a pharmaceutically acceptable salt thereof.

For example, for a 250 kg animal, a preferred formulation may include the following ingredients, in the quantities indicated:

| Ingredient | Amount per Bolus | Preferred Quantity |
| --- | --- | --- |
| Difloxacin HCl | 1000–5000 mg | 1700 mg |
| Binder | 1000–10,000 mg | 3000 mg |
| Disintegrant | 100–1000 mg | 400 mg |
| Lubricant | 50–500 mg | 200 mg |
| Glidant | 100–1000 mg | 200 mg |
| Bulking Agent | 10,000–21,000 mg | q.s. ad 23.0 g |

The proportions of the ingredients may be modified to give compositions with different dosage strengths, without affecting the properties of the composition.

Although the present invention is not limited to single-dosage administration of the composition, it is preferred that the present method consist of orally administering an effective amount of the composition in a single dosage to a ruminant in need thereof. However, the present method may consist essentially of or consist of orally administering the present composition to a ruminant in need thereof as needed to maintain an effective blood level in the ruminant for a length of time sufficient to treat the microbial infection.

The ruminants to whom the present composition is administered include animals of the genera Bos (cows), Ovis (sheep), Capra (goats), Lama (llamas) and Bison (buffalo), preferably Bos. Particularly preferred ruminants include members of the species *Bos taurus, Bos gaurus, Bos javanicus, Bos mutus grunniens, Bos primigenius, Capra hircus, Ovis ammon, Ovis aries, Ovis musimon, Ovis orientalis, Lama guanico* and *Bison bison*, most preferably *Bos taurus*.

In one embodiment, the present method comprises administering the composition to a ruminant in need thereof with the aid of a "balling gun." A balling gun is a tulip-shaped device comprising a tube with one concave, bell-shaped end and a plunger at the opposite end. The composition is placed in the bell end of the balling gun, the bell end of the balling gun is placed into or down the throat of the ruminant, and the plunger is depressed, thus releasing the composition into the throat or esophagus of the ruminant.

Other substances, such as a feed or second active agent (e.g., a nutrient such as a vitamin, essential amino acid, etc.; a second pharmaceutically active compound such as a second antibacterial compound, an antiviral agent or other antimicrobial agent; etc.), may be co-administered with the present composition. A "feed" refers to a commercially available product digestible in ruminants, sold for the purpose of feeding ruminants, and also includes those substances such as hay, grasses, concentrates, etc., grown and/or prepared at the location where the ruminants are kept (e.g., farm) for the purpose of feeding the same to the ruminants. Thus, the present method may further comprise, consist essentially of, or consist of co-administering a feed or second active agent to a ruminant in need thereof.

It is remarkable that the difloxacin hydrochloride is absorbed when administered to an animal having a functioning rumen. Typically, absorption of any drug from the rumen is surprising in view of the fact that the rumen typically contains a large amount of material (e.g., in cows, up to 50 gallons). The material in a functioning rumen is mostly cellulosic in nature, and is able to chemically or physically bind drugs. Rumen microflora are also able to inactivate, bind or chemically alter orally administered drugs. Therefore, it is even more unexpected that the absorption of the drug can be improved by formulating it into an oral composition (particularly a solid composition, and more particularly a bolus).

Another surprising result provided by the present invention is the "extended duration of therapeutic antimicrobial blood levels" properties that the present composition exhibits in ruminating and non-ruminating ruminants. The present composition is able to provide an effective dose of fluoroquinolone antimicrobial over quite an extended period of time (preferably at least 48 hours in a ruminating ruminant, and at least 72 hours in a non-ruminating or pre-ruminating ruminant). Based on results known to the present Inventors prior to the present invention, the length of time during which an effective concentration of a fluoroquinolone antimicrobial is maintained in the blood stream of both ruminating and non-ruminating ruminants by the present composition is unexpected.

Other features of the invention will become apparent in the course of the following descriptions of exemplary embodiments which are given for illustration of the invention and are not intended to be limiting thereof.

EXPERIMENT 1

Experiment 1 tested the plasma concentration of a fluoroquinolone antimicrobial (difloxacin) as a function of time, provided by a solid composition administered to ruminating steers in accordance with two different techniques.

MATERIALS AND METHODS
STUDY DESIGN—PHARMACOKINETICS:

| Treatment Group | n | Route of Admin. | Blood Smp./ Steer | Blood Smp./ Group | Observations |
|---|---|---|---|---|---|
| Difloxacin Suspension (5 mg/kg) | 4 | Gavage | 15 | 60 | Daily |
| Difloxacin capsule (5 mg/kg) | 4 | Per os | 15 | 60 | Daily |

TEST MATERIALS:
  (1) Difloxacin HCl oral suspension; Concentration as free base difloxacin=50 mg/ml
  (2) Difloxacin capsule; Concentration as free base difloxacin=91.64%

TEST ANIMALS:
Ten 12- to 18-month-old steers having an average body weight of approximately 250–300 kg were initially obtained, and eight of the steers were studied. Steers had not been administered drugs or biological agents that could have interfered with the study of the effects of difloxacin. No concomitant medication was administered during the study.

The steers were placed in a single pen, and started on a diet of ad libitum grower ration. Water was offered free choice. The animals were acclimated 7 days prior to the start of the study. Physical examinations were performed on each steer before the start of the study to ensure that they had no clinical or subclinical disease. The steers were observed daily during the test period.

TEST ARTICLE ADMINISTRATION:
Difloxacin oral suspension was administered at 5 mg base activity/kg as a gavage using standard techniques. The difloxacin capsule was administered at 5 mg base activity/kg using standard techniques. Day 0 weights were determined and dosages were based on those weights. Gelatin capsules were prepared at the time of dosing.

BLOOD SAMPLING:
Approximately 10 mL blood samples were collected into EDTA glass evacuated tubes by venipuncture of the left or right jugular veins. Blood samples were harvested at post-injection hours 0, 0.083, 0.25, 0.5, 0.75, 1, 2, 4, 6, 8, 10, 12, 24, 48, and 72.

Following collection, blood samples were chilled on ice. Blood samples were centrifuged at 1500×G for 10 minutes, within one hour of collection. The plasma was pipetted into duplicate vials which were sealed and stored at $\leq -20°$ C. until analysis.

PHARMACOKINETIC ANALYSIS:
The determination of the best fit compartmental model and initial estimates of the model dependent pharmacokinetic parameters of $A_1$, $A_2$, apparent $K_1$ and apparent $K_2$ (Baggot, *Principles of Drug Disposition in Domestic Animals*, W. B. Saunders Co., Philadelphia (1977)) were made using RSTRIP (Fox et al, *RSTRIP*, MicroMath, Inc. (1986)). The procedure used to determine the best fit compartment model involved computing the sum of the squares of the deviations:

The set of parameters obtained that minimized F was chosen as the best estimate. The compartmental model utilized is represented by the general equation:

$$C_p t = A_1 e^{-K_1 t} + A_2 e^{-K_2 t}$$

where $A_1$ and $A_2$ are the time zero plasma drug concentrations, $K_1$ is the apparent rate constant of absorption and $K_2$ is the apparent rate constant of elimination. Respective half-lives were computed from the relationship $t_{1/2} = 0.693$/rate constant. Confidence intervals for the half-lives were computed as described by Bartoszynski et al, Construction of best confidence intervals for half-lives, *Journal of Veterinary Pharmacology and Therapeutics*, 13, 1–6 (1990)).

The plasma concentration-time data were also analyzed using statistical moments (Gibaldi et al, *Pharmacokinetics*, Marcel Dekker Inc., New York (1982)). The system moment mean residence time (MRT) was determined from the equation MRT=AUMC/AUC, where AUMC is the area under the curve of a plot of the product of time and plasma drug concentration-time, from 0 to infinity, and AUC is the area under the concentration-time curve from zero to infinity. The AUC and AUMC were calculated using the method described by Dunne et al, Estimation of noncompartmental parameters: a technical note. *Journal of Pharmacokinetics and Biopharmaceuticals*, 17, 131–137 (1989)).

Mean plasma difloxacin and concentrations at steady-state ($C_{SS,AV}$) were estimated from the relationship:

$$C_{SS,AV} = AUC/\text{dosing interval}$$

For these calculations, it was assumed that the dosing interval was 24 h. Maximum plasma difloxacin concentrations ($C_{max}$), plasma concentrations at 24 hours ($C_{24}$) and times to maximum concentration ($t_{max}$) were determined from the mean values of difloxacin concentration-time curves using four independent observations per post dosing time. All routine statistical methods were described by Snedecor et al, *Statistical Methods*, Iowa State University Press, Ames, Iowa (1982).

Figure 1:
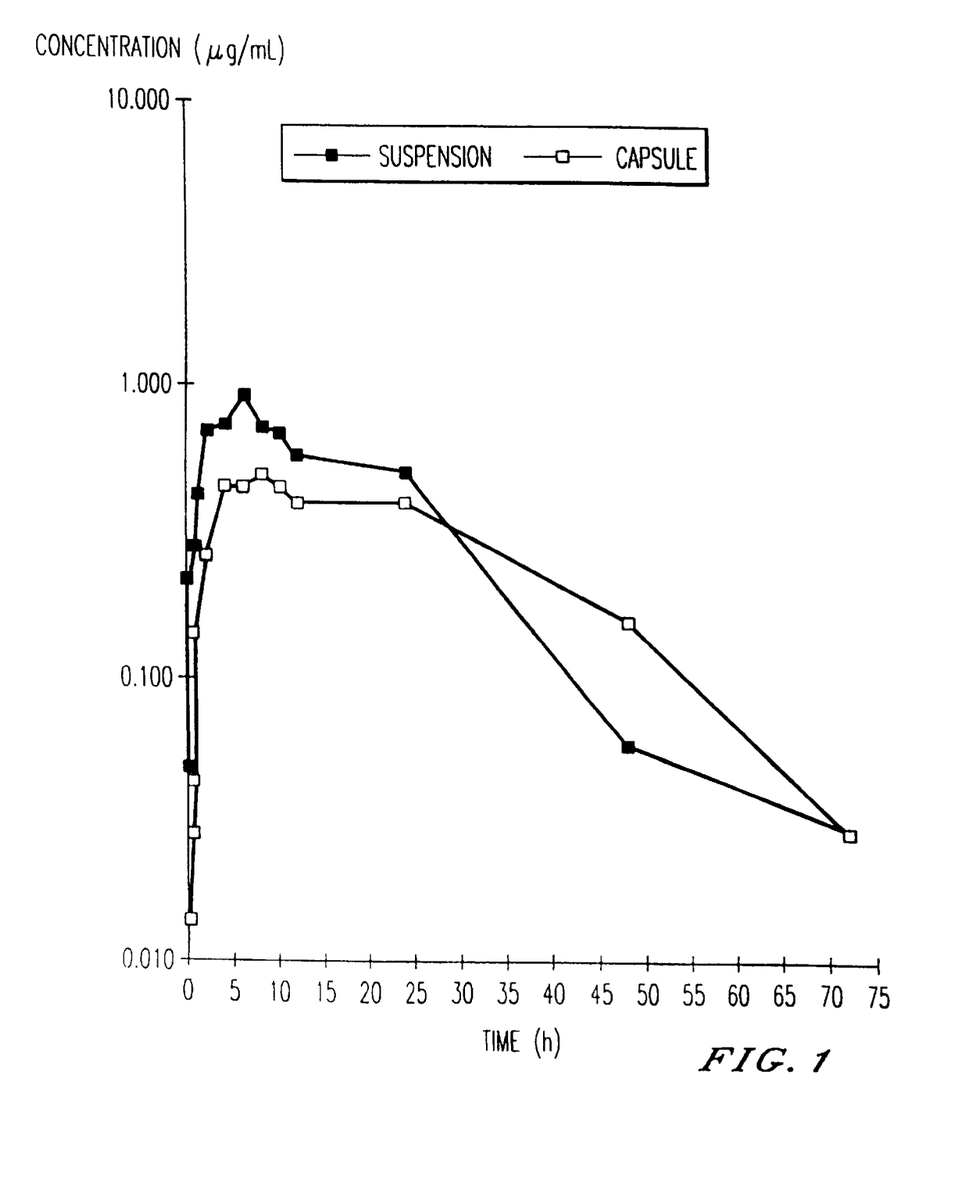
FIG. 1 is a graph showing mean plasma difloxacin concentrations in ruminating cattle after administration of difloxacin (5 mg/kg of body weight) per os (in a capsule) and by gavage (in a suspension)

RESULTS AND DISCUSSION:

Mean plasma difloxacin concentrations in ruminating cattle after administration (5 mg difloxacin/kg of body weight) of a difloxacin capsule per os or suspension by gavage for all sampling periods are presented in Table 1. These values are depicted graphically in FIG. 1. The mean plasma pharmacokinetic parameters calculated from these data are summarized in Table 2.

After oral administration of a single dose (5 mg/kg of body weight) of difloxacin suspension, the absorption of difloxacin in ruminating cattle was rapid. The mean peak plasma concentration was 0.968 μg/mL, occurring 4.667 hours after dosing. The AUC after gavage administration was 25.362 μg·h/mL. The elimination half-life was 18.722 hours. The calculated steady-state concentration based on 24 hour interval dosing was 0.942 μg/mL.

After oral administration of a single dose (5 mg/kg of body weight) of a difloxacin capsule, the absorption of difloxacin in ruminating cattle was not as rapid as the suspension and mean peak plasma concentration was 0.525 μg/mL and occurred 8.0 hours after dosing. The AUC after gavage administration was 20.797 μg·h/mL. The elimination half-life was 21.636 hours. The calculated steady-state concentration based on 24 hour interval dosing was 0.764 μg/mL.

No adverse effects were observed after the administration of either difloxacin formulation.

TABLE 1

Mean plasma difloxacin concentrations in ruminating cattle after administration of a difloxacin capsule peros or suspension by gavage (5 mg difloxacin/kg body weight)

| Postdosing Time [hr] | Suspension Mean* [μg/mL] | Capsule Mean [μg/mL] |
|---|---|---|
| 0 | <.01 | <.01 |
| 0.083 | 0.048 | <.01 |
| 0.25 | 0.220 | 0.014 |
| 0.5 | 0.219 | 0.028 |
| 0.75 | 0.284 | 0.043 |
| 1 | 0.428 | 0.142 |
| 2 | 0.700 | 0.264 |
| 4 | 0.738 | 0.455 |
| 6 | 0.927 | 0.454 |
| 8 | 0.724 | 0.500 |
| 10 | 0.694 | 0.455 |
| 12 | 0.585 | 0.405 |
| 24 | 0.521 | 0.411* |
| 48 | 0.061 | 0.165 |
| 72 | 0.030 | 0.030 |

*Value(s) from three animals.

TABLE 2

Mean plasma pharmacokinetic parameters for difloxacin in ruminating cattle after administration (5 mg difloxacin/kg body weight) of a difloxacin capsule peros or suspension by gavage

| Parameter | Units | Suspension* | Capsule |
|---|---|---|---|
| Compartmental Model | | | |
| $A_1$ | μg/mL | −1.093 | −0.777 |
| Apparent $K_1$ | h⁻¹ | 0.631 | 0.259 |
| Apparent $t(½)_1$ | h | 1.177 | 3.008 |
| $A_2$ | μg/mL | 1.093 | 0.777 |
| Apparent $K_2$ | h⁻¹ | 0.04 | 0.033 |
| Apparent $t(½)_2$ | h | 18.722 | 21.636 |
| Noncompartmental Model | | | |
| $C_{max}$ | μg/mL | 0.968 | 0.525 |
| $C_{24}$ | μg/mL | 0.521 | 0.411 |
| $C_{ss,av}$ | μg/mL | 0.942 | 0.764 |
| $t_{max}$ | h | 4.667 | 8.000 |
| MRT | h | 28.709 | 35.554 |
| AUC (0-t) | μg · h/mL | 22.618 | 18.332 |
| AUC (0-∞) | μg · h/mL | 25.362 | 20.797 |
| AUMC | μg · h²/mL | 727.56 | 756.23 |

*Data from three animals.

The compartmental model is represented by the general equation:

$$C_p t = A_1 e^{-K_1 t} + A_2 e^{-K_2 t}$$

where $A_1$ and $A_2$ refer to time zero plasma drug concentrations; $K_1$ is the apparent rate constant of absorption; $K_2$ is the apparent rate constant of elimination; $t(½)_1$ is the apparent half-life of absorption; and $t(½)_2$ is the apparent half-life of elimination.

The noncompartmental model is based on observations and computations from means of 4 independent sampling units at each of 14 postdosing time periods. $C_{max}$ is the maximum plasma concentration observed; $C_{24}$ is the plasma drug concentration at 24 hours after dosing; $C_{ss,av}$ is the average drug concentration in plasma during a dosing interval at steady state on administering the stated dose every 24 hours; $t_{max}$ is the observed time of peak plasma concentration; MRT refers to the mean residence time; AUC (0–t) is the area under the tissue drug concentration-time curve from zero to time t. AUC (0–∞) is the area under the tissue drug concentration-time curve from zero to infinity. AUMC refers to the area under the curve of a plot of the product of time and plasma drug concentration-time.

The results of this experiment demonstrate that solid compositions (particularly capsules and boluses) of fluoroquinolone antimicrobials or pharmaceutically acceptable salts thereof (particularly difloxacin or an HCl salt thereof) provide surprising absorption and extended duration of therapeutic antimicrobial blood levels properties when administered orally to ruminating ruminants.

EXPERIMENT 2

PHARMACOKINETICS AND TISSUE RESIDUE DEPLETION OF DIFLOXACIN ORAL BOLUS IN FEEDLOT CATTLE

SUMMARY:

Experiment 2 determined the plasma pharmacokinetics and tissue residue depletion in ruminating steers following a single administration of a difloxacin bolus (at a dosage of either 5 or 10 mg free base equivalent/kg body weight).

SAFETY:

There were no adverse affects observed after the administration of the oral difloxacin.HCl boluses.

TEST MATERIALS:

T1 and T2: Difloxacin.HCl bolus, 1134.0 mg base equivalent/bolus (5 mg/kg); T3 and T4: Difloxacin.HCl bolus, 2268.0 mg base equivalent/bolus (10 mg/kg).

STUDY DESIGN:

| Treatment Group | No. of Animals (n) | Dose (mg/kg BW) | Route of Admin. | Blood Smp./ Animal |
|---|---|---|---|---|
| T1 Difloxacin | 3 | 5.0 | Per OS | 21 |
| T2 Difloxacin | 3 | 5.0 | Per OS | 23 |
| T3 Difloxacin | 3 | 10.0 | Per OS | 21 |
| T4 Difloxacin | 3 | 10.0 | Per OS | 23 |

TEST ANIMALS:

Twelve 4- to 8-month-old ruminating steers having an average body weight of approximately 227 kg were studied. Steers had not been administered drugs or biological agents that could have interfered with the study of the effects of difloxacin. No concomitant medication was administered during the study.

Steers were acclimated to the test environment 7 days prior to the start of the study. Physical examinations were performed on each steer before the start of the study to ensure that they had no clinical or subclinical disease. The steers were placed in individual pens and started on a diet of free choice hay. Water was offered free choice.

The steers were observed daily. All steers were sacrificed at the termination of the study.

TEST ARTICLE ADMINISTRATION:

The 12 steers were randomly allocated to treatment. On study day 0, difloxacin was administered orally via a bolus at 5.0 (T1, T2) or 10.0 (T3, T4) mg base equivalent/kg of body weight. Boluses were shaved, as necessary, to more accurately dose the animal at the desired levels, based on the animal's body weight.

BLOOD SAMPLING:

Blood samples were collected in the same manner and volume as in Experiment 1, but at time 0 and at 0.5, 1, 2, 4, 8, 12, 24, 48, 72, 96, 120, 144, 168, 192, 216, 240, 264, 288, 312, 336, 504 and 672 hours after test article administration. Following collection, blood samples were treated and stored in the same manner as in Experiment 1.

SCHEDULE:

| Day | Activity(ies) |
|---|---|
| −7 | Cattle received |
| 0 | All cattle dosed perorally |
| 0–14, 21, 28 | Cattle bled |
| 0–28: | Daily observations made |

PHARMACOKINETIC RESULTS AND DISCUSSION:

Pharmacokinetic analysis was performed as in Experiment 1.

Figure 2:
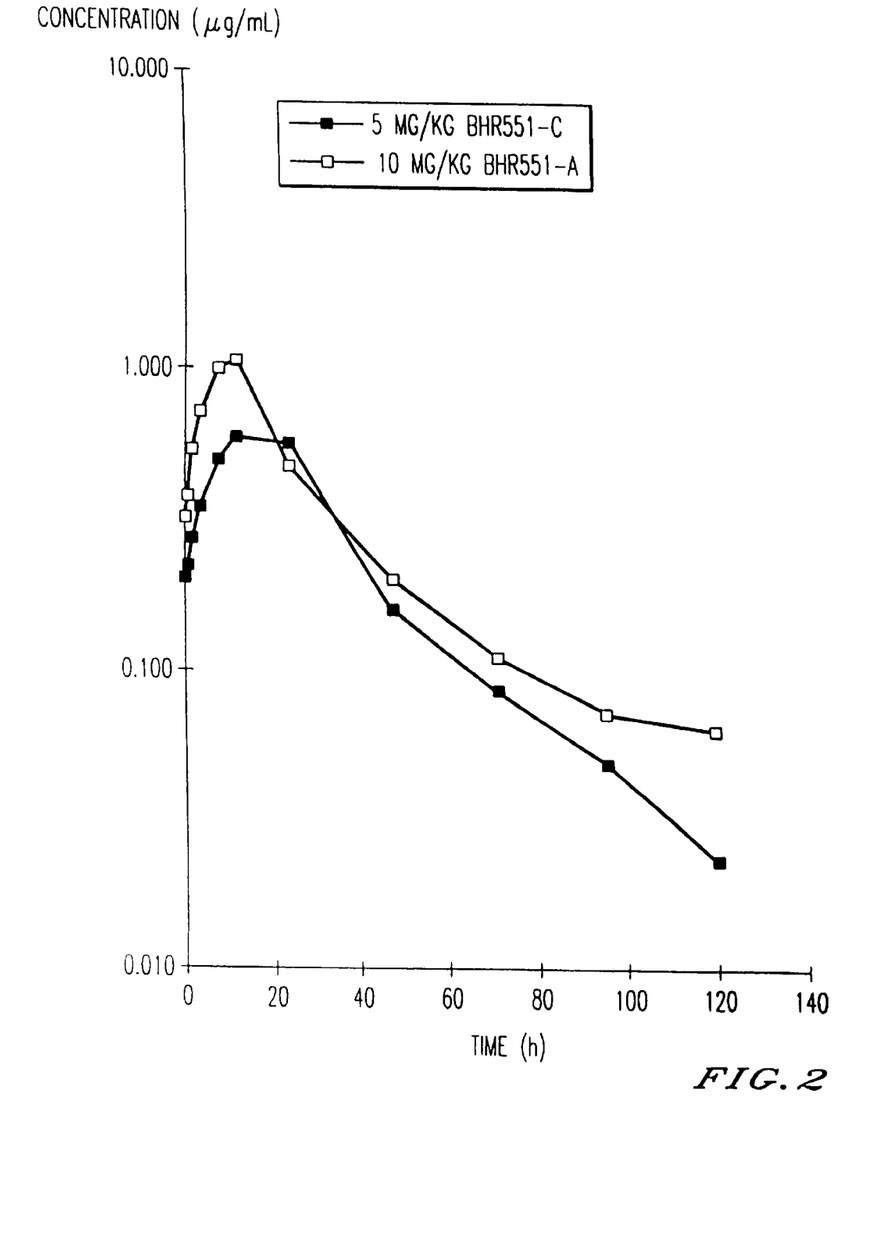
FIG. 2 is a graph showing the concentration of difloxacin (in $\mu g/mL$) against time (in h) for two examples of the present oral veterinary bolus (5 and 10 mg/kg)

Mean plasma difloxacin concentrations in steers following a single oral administration of a difloxacin bolus (5 and 10 mg base equivalent/kg body weight) are presented in Table 3. These values are depicted graphically in FIG. 2. The mean plasma pharmacokinetic parameters calculated from these data are summarized in Table 4.

After oral administration of 5 mg base equivalent/kg body weight of difloxacin HCl, the absorption of difloxacin was rapid and sustained. Mean peak plasma concentration was 0.682 µg/mL, occurring 17.3 hours after dosing. The AUC (0–t) after oral administration was 24.378 µg·h/mL. The elimination half-life was 17.210 hours. The calculated steady-state concentration based on 24 hour interval dosing was 1.064 µg/mL.

After oral administration of 10 mg base equivalent/kg body weight of difloxacin HCl, the absorption of difloxacin was rapid and sustained. Mean peak plasma concentration was 1.166 µg/mL, occurring 10.0 hours after dosing. The AUC (0–t) after oral administration was 30.848 µg·h/mL. The elimination half-life was 14.170 hours. The calculated steady-state concentration based on 24 hour interval dosing was 1.297 µg/mL.

TABLE 3

Mean plasma difloxacin concentrations in calves receiving a single 5 mg/kg or 10 mg/kg oral dose

| Postdosing Time (hr) | T1 or T2 BHR551-C Mean (µg/mL) | T3 or T4 BHR551-A Mean (µg/mL) |
|---|---|---|
| 0 | <0.010 | <0.010 |
| 0.5 | 0.201 | 0.318 |
| 1 | 0.220 | 0.373 |
| 2 | 0.272 | 0.528 |
| 4 | 0.345 | 0.714 |
| 8 | 0.494 | 0.996 |
| 12 | 0.587 | 1.057 |
| 24 | 0.558 | 0.473 |
| 48 | 0.160 | 0.201 |
| 72 | 0.087 | 0.112 |
| 96 | 0.049* | 0.073*** |
| 120 | 0.023** | 0.064**** |
| 144 | <0.010 | <0.010 |
| 168 | <0.010 | <0.010 |
| 192 | <0.010 | <0.010 |
| 216 | <0.010 | <0.010 |
| 240 | <0.010 | <0.010 |
| 264 | <0.010 | <0.010 |
| 288 | <0.010 | <0.010 |
| 312 | <0.010 | <0.010 |
| 336 | <0.010 | <0.010 |
| 504 | <0.010 | <0.010 |
| 672 | <0.010 | <0.010 |

*Mean of three animals
**Value from one animal
***Mean of five animals
****Mean of four animals

TABLE 4

Mean plasma pharmacokinetic parameters for difloxacin in calves receiving a single 5 mg/kg or 10 mg/kg oral dosage

| Parameter | Units | T1 and T2 | T3 and T4 |
|---|---|---|---|
| Compartmental Model | | | |
| $A_1$ | µg/mL | −2.548 | −2.278 |
| Apparent $K_1$ | $h^{-1}$ | 0.165 | 0.265 |
| Apparent $t(½)_1$ | h | 5.550 | 3.149 |
| $A_2$ | µg/mL | 2.548 | 2.278 |
| Apparent $K_2$ | $h^{-1}$ | 0.041 | 0.052 |
| Apparent $t(½)_2$ | h | 17.210 | 14.170 |
| Noncompartmental Model | | | |
| $C_{max}$ | µg/mL | 0.682 | 1.166 |
| $C_{24}$ | µg/mL | 0.558 | 0.473 |
| $C_{ss,av}$ | µg/mL | 1.064 | 1.297 |
| $t_{max}$ | h | 17.333 | 10.000 |
| MRT (0-t) | h | 29.003 | 23.919 |
| AUC (0-t) | µg · h/mL | 24.378 | 30.848 |
| AUC (0-∞) | µg · h/mL | 25.534 | 31.126 |
| AUMC (0-t) | µg · $h^2$/mL | 718.752 | 756.475 |

The results of this experiment demonstrate that solid compositions (particularly boluses) of fluoroquinolone antimicrobials or pharmaceutically acceptable salts thereof (particularly difloxacin or an HCl salt thereof) provide surprising absorption and extended duration of therapeutic antimicrobial blood levels properties when orally administered to ruminating ruminants.

EXPERIMENT 3

PHARMACOKINETICS OF A DIFLOXACIN ORAL BOLUS IN FEEDLOT CATTLE

SUMMARY:

Experiment 3 determined the plasma pharmacokinetics in ruminating steers in a feedlot environment following a single administration of a difloxacin bolus (at a dosage of either 5 or 10 mg free base equivalent/kg body weight).

TEST MATERIALS:

T1: Difloxacin.HCl bolus, 1277.0 mg base equivalent/bolus (5 mg/kg); T2: Difloxacin.HCl bolus, 2518.0 mg base equivalent/bolus (10 mg/kg).

STUDY DESIGN:

| Treatment Group | No. of Animals | Dose (mg/kg BW) | Route of Admin. | Blood Smp./ Animal |
|---|---|---|---|---|
| T1 Difloxacin | 6 | 5.0 | Per OS | 17 |
| T2 Difloxacin | 6 | 10.0 | Per OS | 17 |

TEST ANIMALS:

Twelve 5- to 9-month-old ruminating steers having an average body weight of approximately 212 kg were studied. Steers had not been administered drugs or biological agents that could have interfered with the study of the effects of difloxacin. No concomitant medication was administered during the study.

Steers were acclimated to the test environment 7 days prior to the start of the study. Physical examinations were performed on each steer before the start of the study to ensure that they had no clinical or subclinical disease. The steers were group-housed with approximately 2.3 feet of bunk space and 276.6 square feet per head. The steers had water and a basal ration ad libitum. The steers had fully functioning rumens. The steers were observed daily throughout the test period.

TEST ARTICLE ADMINISTRATION:

The 12 steers were randomly allocated to treatment. On study day 0, difloxacin was administered orally via a bolus at 5.0 (T1) or 10.0 (T2) mg base equivalent/kg of body weight. Boluses were shaved, as necessary, to more accurately dose the animal at the desired levels, based on the animal's body weight.

BLOOD SAMPLING:

Blood samples were collected in the same manner and volume as in Experiment 1, but at time 0 and at 1, 2, 4, 6, 9, 11, 13, 15, 18, 20, 24, 36, 48, 72, 120 and 168 hours after test article administration. Following collection, blood samples were treated and stored in the same manner as in Experiment 1.

Cattle plasma samples were analyzed for difloxacin using a protein precipitation and ultrafiltration process followed by high performance liquid chromatography (HPLC) with fluorescence detection. An internal standard (A-56681.1 hydrochloride, obtained from Abbott Laboratories) was added to the plasma followed by a large volume of base and then a small volume of acid. After centrifugation to precipitate proteins, the supernatant was placed above an ultrafiltration membrane and centrifuged again. The ultrafiltrate was injected into the liquid chromatograph.

SCHEDULE:

| Day | Activity(ies) |
|---|---|
| −7 | Potential study cattle selected (approximately 15); Physical examinations given; Steers identified |
| −7–0 | Steers acclimated |
| −1 | Body weight measured, physical examinations given; Dosages prepared; Scales for boluses and for steer body weight validated; Animals randomized |
| 0 | All cattle dosed perorally |
| 0 to 7 | Cattle bled |

PHARMACOKINETIC RESULTS AND DISCUSSION:

Pharmacokinetic analysis was performed as in Experiment 1.

Figure 3:
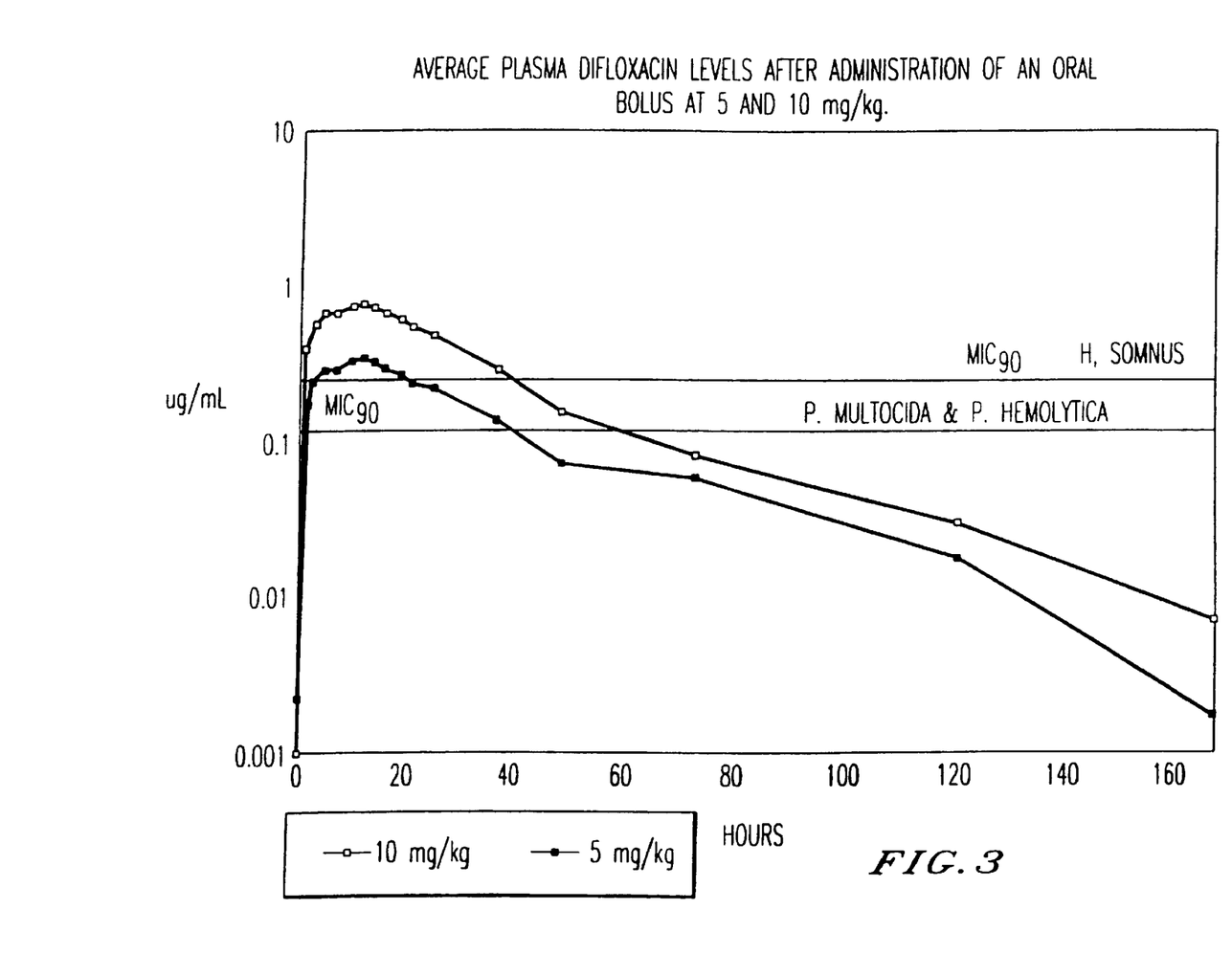
FIG. 3 is a graph showing average plasma difloxacin concentrations in ruminating cattle after administration of a difloxacin bolus (5 mg/kg or 10 mg/kg of body weight) as a function of time, with the $MIC_{90}$ levels against *Haemophilus somnus*, *Pasteurella multocida* and *Pasteurella hemolytica* provided for reference.

Mean plasma difloxacin concentrations in steers following a single oral administration of a difloxacin bolus (5 and 10 mg base equivalent/kg body weight) are presented in Table 5 and are depicted graphically in FIG. 3. The mean plasma pharmacokinetic parameters calculated from these data are summarized in Table 6.

After oral administration of 5 mg base equivalent/kg body weight of difloxacin HCl, the absorption of difloxacin was rapid and sustained, resulting in persistently high plasma difloxacin concentrations. Mean peak plasma concentration was 0.35 µg/mL, occurring~11 hours after dosing. The $AUC_{(0-168h)}$ (area under the plasma difloxacin concentration versus time curve from time 0 to 168 hours) after oral administration was 13.89 µg·h/mL. The apparent elimination half-life was 21.44 hours. The calculated steady-state concentration based on 24 hour interval dosing was 0.578 µg/mL.

After oral administration of 10 mg base equivalent/kg body weight of difloxacin HCl, the absorption of difloxacin was rapid and sustained, resulting in persistently high plasma difloxacin concentrations. Mean peak plasma concentration was 0.77 µg/mL, occurring~11 hours after dosing. The $AUC_{(0-168h)}$ after oral administration was 28.71 µg·h/mL. The apparent elimination half-life was~19.39 hours. The calculated steady-state concentration based on 24 hour interval dosing was 1.196 µg/mL.

The compartmental model is represented by the equation given in Experiment 1 above, and the noncompartmental model is based on observations and computations from means of 6 independent sampling units at each of the 17 post-dosing time periods. In Table 6, "AUC" was calculated using the trapezoidal method from time 0–168 hours, and the $C_{max}$ is the observed $C_{max}$. The "half life" was calculated using RSTRIP II exponential stripping and parameter estimation software (produced by MICROMATH™ Scientific Software, Salt Lake City, Utah).

TABLE 5

Raw data summary and mean plasma difloxacin concentrations in 5- to 9-month-old steers receiving a single 5 mg/kg or 10 mg/kg oral dose

| Time (hours post dose) | Cattle Identification 10 mg/kg | | | | | | 5 mg/kg | | | | | | Mean 10 mg/kg | Mean 5 mg/kg |
|---|---|---|---|---|---|---|---|---|---|---|---|---|---|---|
| | 761 | 760 | 754 | 770 | 767 | 777 | 773 | 768 | 756 | 771 | 769 | 779 | | |
| 0 | 0.00 | 0.00 | 0.00 | 0.00 | 0.00 | 0.00 | 0.00 | 0.00 | 0.00 | 0.00 | 0.01 | 0.00 | 0.00 | 0.00 |
| 1 | 0.45 | 0.26 | 0.23 | 0.40 | 0.55 | 0.47 | 0.28 | 0.09 | 0.17 | 0.23 | 0.14 | 0.12 | 0.39 | 0.17 |
| 2 | 0.53 | 0.52 | 0.43 | 0.66 | 0.73 | 0.55 | 0.38 | 0.19 | 0.24 | 0.25 | 0.26 | 0.16 | 0.57 | 0.25 |
| 4 | 0.59 | 0.66 | 0.60 | 0.73 | 0.86 | 0.59 | 0.36 | 0.30 | 0.31 | 0.27 | 0.32 | 0.18 | 0.67 | 0.29 |
| 6 | 0.63 | 0.73 | 0.62 | 0.68 | 0.83 | 0.53 | 0.33 | 0.32 | 0.33 | 0.27 | 0.30 | 0.20 | 0.67 | 0.29 |
| 9 | 0.67 | 0.83 | 0.69 | 0.73 | 0.92 | 0.63 | 0.34 | 0.39 | 0.40 | 0.24 | 0.35 | 0.25 | 0.74 | 0.33 |
| 11 | 0.71 | 0.82 | 0.72 | 0.78 | 0.94 | 0.63 | 0.35 | 0.38 | 0.42 | 0.28 | 0.38 | 0.26 | 0.77 | 0.35 |
| 13 | 0.66 | 0.83 | 0.70 | 0.74 | 0.83 | 0.62 | 0.35 | 0.38 | 0.37 | 0.27 | 0.33 | 0.25 | 0.73 | 0.33 |
| 15 | 0.61 | 0.81 | 0.61 | 0.76 | 0.69 | 0.57 | 0.33 | 0.33 | 0.31 | 0.27 | 0.30 | 0.24 | 0.68 | 0.30 |
| 18 | 0.57 | 0.71 | 0.59 | 0.67 | 0.63 | 0.51 | 0.30 | 0.28 | 0.31 | 0.25 | 0.26 | 0.23 | 0.61 | 0.27 |
| 20 | 0.56 | 0.65 | 0.49 | 0.60 | 0.51 | 0.44 | 0.25 | 0.21 | 0.29 | 0.22 | 0.22 | 0.21 | 0.54 | 0.24 |
| 24 | 0.49 | 0.62 | 0.43 | 0.55 | 0.43 | 0.37 | 0.24 | 0.22 | 0.25 | 0.23 | 0.20 | 0.19 | 0.48 | 0.22 |
| 36 | 0.31 | 0.32 | 0.29 | 0.34 | 0.24 | 0.24 | 0.12 | 0.15 | 0.16 | 0.14 | 0.14 | 0.12 | 0.29 | 0.14 |
| 48 | 0.19 | 0.18 | 0.15 | 0.17 | 0.12 | 0.12 | 0.06 | 0.07 | 0.08 | 0.08 | 0.09 | 0.06 | 0.16 | 0.07 |
| 72 | 0.11 | 0.09 | 0.08 | 0.09 | 0.06 | 0.06 | 0.05 | 0.05 | 0.12 | 0.05 | 0.05 | 0.04 | 0.08 | 0.06 |
| 120 | 0.06 | 0.03 | 0.02 | 0.03 | 0.03 | 0.02 | 0.01 | 0.02 | 0.02 | 0.02 | 0.02 | 0.01 | 0.03 | 0.02 |
| 168 | 0.02 | 0.01 | 0.00 | 0.01 | 0.00 | 0.00 | 0.00 | 0.00 | 0.00 | 0.01 | 0.00 | 0.00 | 0.01 | 0.00 |

TABLE 6

Pharmacokinetic parameter summary for difloxacin in 5- to 9-month-old steers receiving a single 5 mg/kg or 10 mg/kg oral dosage

| Animal | Dose | AUC | Cmax | Half Life | P. multocida and F. hemolytica | | H. somnus | |
|---|---|---|---|---|---|---|---|---|
| | | | | | Cmax/MIC90 Ratio | AUC/MIC90 Ratio | Cmax/MIC90 Ratio | AUC/MIC90 Ratio |
| 773 | 5.00 | 13.69 | 0.38 | 20.57 | 3.20 | 114.08 | 1.54 | 54.76 |
| 768 | 5.00 | 14.01 | 0.39 | 14.70 | 3.23 | 116.71 | 1.55 | 56.02 |
| 756 | 5.00 | 17.62 | 0.42 | 22.24 | 3.46 | 146.79 | 1.66 | 70.46 |
| 771 | 5.00 | 13.44 | 0.28 | 32.06 | 2.33 | 112.00 | 1.12 | 53.76 |
| 769 | 5.00 | 13.94 | 0.38 | 19.26 | 3.17 | 116.13 | 1.52 | 55.74 |
| 779 | 5.00 | 10.63 | 0.26 | 19.81 | 2.17 | 88.58 | 1.04 | 42.52 |
| Average | | 13.89 | 0.35 | 21.44 | 2.93 | 115.72 | 1.41 | 55.54 |
| 761 | 10.00 | 31.43 | 0.71 | 26.89 | 5.91 | 261.88 | 2.83 | 125.70 |
| 760 | 10.00 | 32.27 | 0.83 | 16.82 | 6.94 | 268.92 | 3.33 | 129.08 |
| 754 | 10.00 | 26.12 | 0.72 | 17.26 | 5.99 | 217.67 | 2.87 | 104.48 |
| 770 | 10.00 | 31.25 | 0.78 | 21.32 | 6.50 | 260.42 | 3.12 | 125.00 |
| 767 | 10.00 | 28.19 | 0.94 | 14.25 | 7.85 | 234.92 | 3.77 | 112.76 |
| 777 | 10.00 | 23.02 | 0.63 | 19.79 | 5.25 | 191.79 | 2.52 | 92.06 |
| Average | | 28.71 | 0.77 | 19.39 | 6.41 | 239.26 | 3.08 | 114.85 |

AUC = trapezoidal rule 0 to time t (t = 168 hours)
MIC90 = 0.12 for P. multocida & P. hemolytica
MIC90 = 0.25 for H. somnus The results of this experiment demonstrate that solid compositions (particularly boluses) of fluoroquinolone antimicrobial agents or pharmaceutically acceptable salts thereof (particularly difloxacin or an HCl salt thereof) provide surprising absorption and extended duration of therapeutic antimicrobial blood level properties when orally administered to ruminating animals.

EXPERIMENT 4

PHARMACOKINETICS OF A DIFLOXACIN ORAL BOLUS IN NON-RUMINATING VEAL CALVES

SUMMARY:

Experiment 4 determined the plasma pharmacokinetics in non-ruminating, non-neonate "veal" calves following a single administration of a difloxacin bolus (at a dosage of either 5 or 10 mg free base equivalent/kg body weight).

TEST MATERIALS:

T1: Difloxacin.HCl bolus, 226.8 mg base equivalent/bolus (5 mg/kg); T2: Difloxacin.HCl bolus, 453.6 mg base equivalent/bolus (10 mg/kg).

STUDY DESIGN:

| Treatment Group | No. of Animals | Dose (mg/kg BW) | Route of Admin. | Blood Smp./ Animal |
|---|---|---|---|---|
| T1 Difloxacin | 3 | 5.0 | Per OS | 18 |
| T2 Difloxacin | 3 | 10.0 | Per OS | 18 |

TEST ANIMALS:

Six 3-week to 1-month-old veal calves having an average body weight of approximately 51.2 kg were studied. The animals had not been administered drugs or biological agents that could have interfered with the effects of difloxacin. No concomitant medication was administered during the study.

Calves were acclimated to the test environment 7 days prior to the start of the study. Physical examinations were performed on each calf before the start of the study to ensure that they had no clinical or subclinical disease. The calves were individually housed, with approximately 48 square feet per head. The calves were given water ad libitum and were fed a commercial milk replacer, according to label directions. The calves did not have functioning rumens. The calves were observed daily throughout the test period.

TEST ARTICLE ADMINISTRATION:

The six calves were randomly allocated to treatment. On study day 0, difloxacin was administered orally via a bolus at 5.0 (T1) or 10.0 (T2) mg based equivalent/kg of body weight. Boluses were shaved, as necessary, to more accurately dose the animal at the desired levels based on the animal's body weight.

BLOOD SAMPLING:

Blood samples were collected in the same manner and volume as in Experiment 1, but at time 0 and at 1, 4, 7, 10, 12, 15, 18, 21, 24 and 36 hours and at 2, 3, 4, 5, 6, 7 and 14 days after test article administration. Following collection, blood samples were treated and stored in the same manner as in Experiment 1.

Calf plasma samples were analyzed for difloxacin in the same manner as Experiment 3, and pharmacokinetic analysis was conducted in the same manner as Experiment 1. The average difloxacin plasma levels after oral administration of either bolus are presented graphically in FIG. 3. The $MIC_{90}$ levels of the bacteria H. somnus (0.25 µg/mL), P. multocida and P. hemolytica (both 0.12 µg/mL) are presented in the graph for reference.

SCHEDULE:

| Day | Activity(ies) |
|---|---|
| −14 | Calves acquired, vaccinated, given physical examinations and identified; status of passive transfer assessed |
| −7 | Calves weighed and randomized |

-continued

| Day | Activity(ies) |
|---|---|
| −1 | Calf body weight determined, physical examinations given |
| 0 | All calves dosed perorally |
| 0–14 | Samples collected and daily observations made |

PHARMACOKINETIC RESULTS AND DISCUSSION:

Pharmacokinetic analysis was performed as in Experiment 1.

Figure 4:
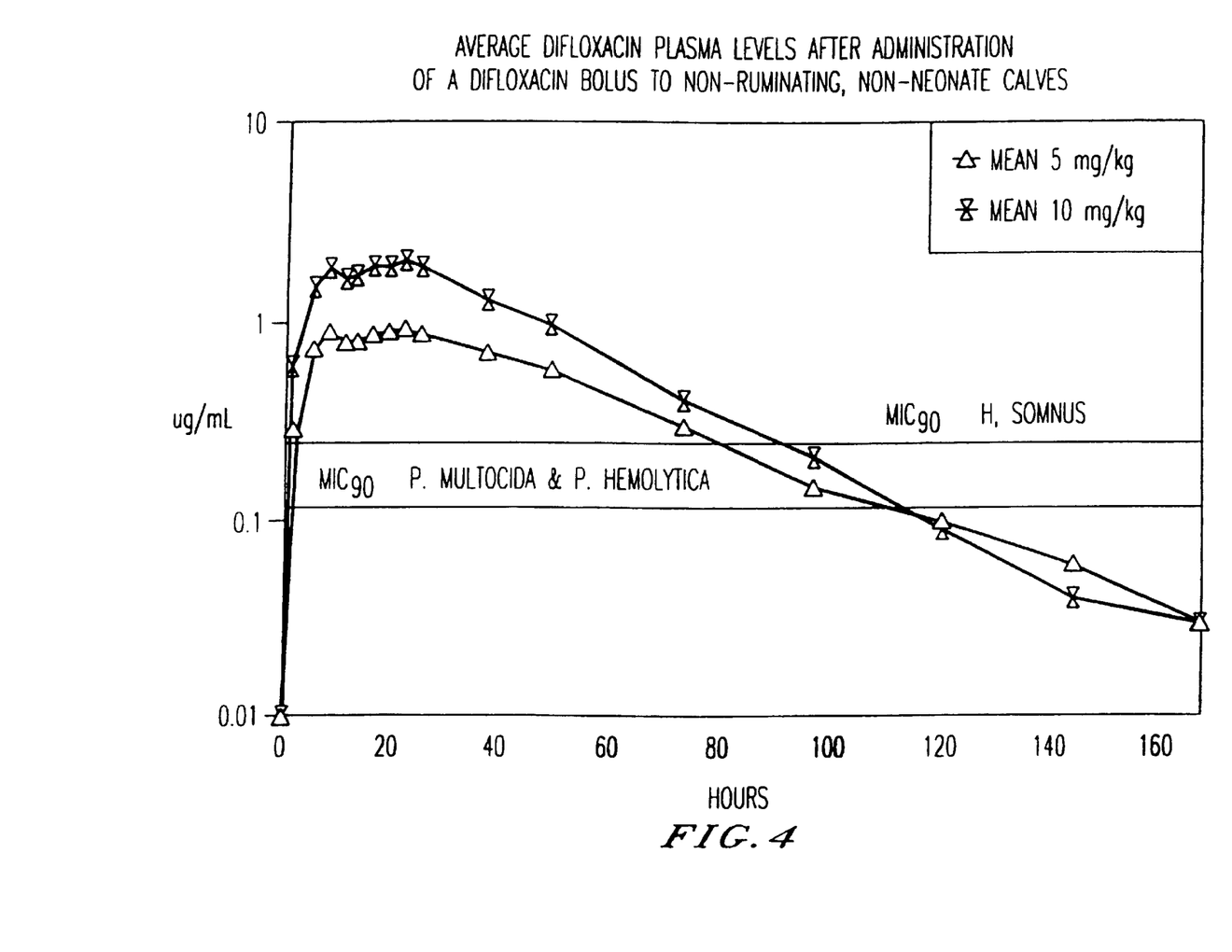
FIG. 4 is a graph plotting the average plasma difloxacin concentration (in $\mu g/mL$) in pre-ruminating ruminants as a function of time (in h) for two examples of the present oral veterinary composition (5 and 10 mg/kg) with the $MIC_{90}$ levels against *H. somnus*, *P. multocida* and *P. hemolytica* provided for reference.

A raw data summary and the mean plasma difloxacin concentrations in calves following a single oral administration of a difloxacin bolus (5 and 10 mg base equivalent/kg body weight) are presented in Table 7 and depicted graphically in FIG. 4. The mean plasma pharmacokinetic parameters calculated from these data are summarized in Table 8.

After oral administration of 5 mg base equivalent/kg body weight of difloxacin HCl, the absorption of difloxacin was rapid and sustained, resulting in persistently high plasma difloxacin concentrations. Mean peak plasma concentration was 0.92 µg/mL, occurring~15.33 hours after dosing. The $AUC_{(0-168h)}$ (area under the plasma difloxacin concentration versus time curve from time 0 to 168 hours) after oral administration was 62.30 µg·h/mL. The apparent elimination half-life was 36.09 hours. The calculated steady-state concentration based on 24 hour interval dosing was 2.596 µg/mL.

After oral administration of 10 mg base equivalent/kg body weight of difloxacin HCl, the absorption of difloxacin was rapid and sustained, resulting in persistently high plasma difloxacin concentrations. Mean peak plasma concentration was 2.03 µg/mL, occurring~16.33 hours after dosing. The $AUC_{(0-168h)}$ after oral administration was 106.32 µg·h/mL. The apparent elimination half-life was~24.36 hours. The calculated steady-state concentration based on 24 hour interval dosing was 4.43 µg/mL.

The compartmental model is represented by the equation given in Experiment 1 above, and the noncompartmental model is based on observations and computations from means of 3 independent sampling units at each of 18 postdosing time periods. In Table 8, "AUC," $C_{max}$ and "half life" are determined as described in Experiment 3. $C_{max}/MIC_{90}$ and $AUC/MIC_{90}$ ratios and average values are presented in Table 7 for each of the animals tested, with reference to the above-described bacteria.

The results of this experiment demonstrate that solid compositions (particularly boluses) of difloxacin or an HCl salt thereof provide surprising extended duration of therapeutic antimicrobial blood level properties when orally administered to pre-ruminating or non-ruminating ruminants.

TABLE 7

Raw data summary and mean plasma difloxacin concentrations in veal calves receiving a single 5 mg/kg or 10 mg/kg oral dose Cattle Identification, levels converted to µg/mL

| | 5 mg/kg | | | 10 mg/kg | | | Average | Average |
|---|---|---|---|---|---|---|---|---|
| Time | 201 | 206 | 207 | 203 | 205 | 202 | 5 mg/kg | 10 mg/kg |
| 0 | 0.00 | 0.00 | 0.00 | 0.00 | 0.00 | 0.00 | 0.00 | 0.00 |
| 1 | 0.32 | 0.48 | 0.06 | 0.64 | 0.67 | 0.48 | 0.29 | 0.60 |
| 4 | 1.06 | 0.78 | 0.39 | 1.61 | 1.72 | 1.12 | 0.74 | 1.49 |
| 7 | 1.56 | 0.69 | 0.45 | 1.96 | 2.11 | 1.47 | 0.90 | 1.85 |
| 10 | 1.21 | 0.71 | 0.49 | 1.60 | 1.68 | 1.61 | 0.80 | 1.63 |
| 12 | 1.20 | 0.71 | 0.52 | 1.57 | 1.69 | 1.89 | 0.81 | 1.72 |
| 15 | 1.22 | 0.79 | 0.61 | 1.69 | 1.85 | 2.15 | 0.87 | 1.90 |
| 18 | 1.23 | 0.76 | 0.71 | 1.65 | 1.76 | 2.22 | 0.90 | 1.88 |
| 21 | 1.26 | 0.77 | 0.73 | 1.63 | 2.13 | 2.32 | 0.92 | 2.03 |
| 24 | 1.12 | 0.76 | 0.72 | 1.43 | 1.90 | 2.30 | 0.87 | 1.88 |
| 36 | 0.95 | 0.55 | 0.62 | 0.81 | 1.34 | 1.68 | 0.71 | 1.28 |
| 48 | 0.68 | 0.51 | 0.55 | 0.50 | 1.19 | 1.22 | 0.58 | 0.97 |
| 72 | 0.31 | 0.26 | 0.33 | 0.30 | 0.46 | 0.47 | 0.30 | 0.41 |
| 96 | 0.15 | 0.14 | 0.15 | 0.13 | 0.20 | 0.30 | 0.15 | 0.21 |
| 120 | 0.06 | 0.08 | 0.15 | 0.06 | 0.08 | 0.13 | 0.10 | 0.09 |
| 144 | 0.03 | 0.05 | 0.10 | 0.02 | 0.04 | 0.06 | 0.06 | 0.04 |
| 168 | 0.02 | 0.03 | 0.05 | 0.01 | 0.02 | 0.04 | 0.03 | 0.03 |
| 336 | 0.00 | 0.01 | 0.00 | 0.00 | 0.00 | 0.00 | 0.00 | 0.00 |

TABLE 8

Pharmacokinetic parameter summary for difloxacin in veal calves receiving a single 5 mg/kg or 10 mg/kg oral dosage
Pharmacokinetic Parameter Summary

| | | | | | | | | P. multocida and P. hemolytics | | H somnus | |
|---|---|---|---|---|---|---|---|---|---|---|---|
| | | | | | | | | MIC90 = 0.12 | | MIC90 = 0.25 | |
| Dose | Animal ID | Observed Cmax | Calculated Cmax | Observed Tmax | Calculated Tmax | AUC | Half Life | Observed Cmax MIC90 Ratio | AUC MIC90 Ratio | Observed Cmax/MIC90 Ratio | AUC MIC90 Ratio |
| 5 mg/kg | 201 | 156 | 1.36 | 7.00 | 10.58 | 74.41 | 30.57 | 13.03 | 620.04 | 6.25 | 297.62 |
| | 206 | 0.79 | 0.83 | 18.00 | 5.64 | 54.91 | 44.33 | 6.58 | 457.58 | 3.16 | 219.64 |
| | 207 | 0.73 | 0.69 | 21.00 | 23.59 | 57.58 | 33.38 | 6.08 | 479.79 | 2.92 | 230.30 |
| | Average | 0.92 | 0.96 | 15.33 | 13.27 | 62.30 | 36.09 | 7.65 | 519.14 | 3.67 | 249.19 |
| 10 mg/kg | 203 | 1.96 | 1.86 | 7.00 | 8.74 | 78.58 | 22.14 | 16.36 | 654.83 | 7.85 | 314.32 |
| | 205 | 2.13 | 2.17 | 21.00 | 19.60 | 26.56 | 16.78 | 17.74 | 1054.67 | 8.52 | 506.24 |
| | 202 | 2.32 | 2.03 | 21.00 | 9.98 | 113.83 | 34.17 | 19.32 | 948.58 | 9.27 | 455.32 |
| | Average | 2.03 | 2.02 | 16.33 | 12.77 | 106.32 | 24.36 | 16.88 | 886.03 | 8.10 | 425.29 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A veterinary composition comprising 0.4 to 40 mg/kg difloxacin or a pharmaceutically effective salt thereof and an orally acceptable inert carrier wherein said composition provides therapeutic antimicrobial blood levels of the difloxacin for a sufficient length of time effective to treat a microbial infection in the ruminating or pre-ruminating animal.

2. The veterinary composition of claim 1, in a solid dosage form selected from the group consisting of a capsule, a tablet, a pill, a powder, a granule, an effervescing granule, a gel, a paste, a troche and a pastille.

3. The veterinary composition of claim 1, in the form of an oral bolus.

4. A method of treating microbial infection in a ruminating or pre-ruminating ruminant, comprising orally administering to the ruminant a veterinary composition which comprises a dosage of difloxacin or a pharmaceutically effective salt thereof and a pharmaceutically acceptable, orally acceptable inert carrier wherein the composition provides therapeutic antimicrobial blood levels of said fluoroquinolone effective to treat a microbial infection in the ruminant.

5. A veterinary composition for treating microbial infection in a ruminating or pre-ruminating ruminant, comprising a dosage of difloxacin or a pharmaceutically effective salt thereof and a pharmaceutically acceptable, orally acceptable inert carrier wherein the composition provides therapeutic antimicrobial blood levels of said difloxacin effective to treat a microbial infection in the ruminant for at least 24 hours.

6. The veterinary composition of claim 1, wherein said length of time is at least 24 hours.

7. The veterinary composition of claim 1, wherein said length of time is at least 48 hours.

8. A method of treating microbial infection in a ruminating or pre-ruminating ruminant, comprising orally administering to the ruminant a veterinary composition which comprises a dosage of fluoroquinolone or a pharmaceutically effective salt thereof and a pharmaceutically acceptable, orally acceptable inert carrier wherein the composition provides therapeutic antimicrobial blood levels of said fluoroquinolone effective to treat a microbial infection in the ruminant and coadministering a second active agent to said ruminant.

9. A method of treating microbial infection in a ruminating or pre-ruminating ruminant, comprising orally administering the veterinary composition of claim 1 to the ruminant as needed to maintain an effective blood level in said ruminant for at least 24 hours to effectively treat a microbial infection.

10. The veterinary composition of claim 1, wherein said veterinary composition is in a liquid dosage form selected from the group consisting of an emulsion, a solution, a suspension, a syrup and an elixir.

11. The veterinary composition of claim 5, further comprising a second active agent.

12. The veterinary composition of claim 5, wherein said ruminant is a member of a genus selected from the group consisting of Bos, Ovis, Capra, Lama, and Bison.

13. The veterinary composition of claim 5, wherein said ruminant is a member of the genus Bos.

14. The method of claim 4, wherein said ruminant is a member of a genus selected from the group consisting of Bos, Ovis, Capra, Lama and Bison.

15. The method of claim 14, wherein said ruminant is a member of the genus Bos.

16. The method of claim 15, wherein said ruminant is a member of the species *Bos taurus*.

17. The method of claim 4, wherein said microbial infection is caused by at least one gram-positive or gram-negative microorganism selected from the group consisting of Staphylococcus, Lactobacillus, Streptococcus, Sarcina, Escherichia, Enterobacter, Klebsiella, Pseudomonas, Acinetobacter, Proteus, Citrobacter, Nisseria, Bacillus, Bacteroides, Peptococcus, Clostridium, Salmonella, Shigella, Serratia, Haemophilus, Pasteurella and Brucella.

18. The veterinary composition of claim 5, wherein said ruminant is a member of the species *Bos taurus*.

19. The veterinary composition of claim 5, wherein the microbial infection is caused by one or more of Staphylococcus, Lactobacillus, Streptococcus, Sarcina, Escherichia, Enterobacter, Klebsiella, Pseudomonas, Acinetobacter, Proteus, Citrobacter, Nisseria, Bacillus, Bacteroides, Peptococcus, Clostridium, Salmonella, Shigella, Serratia, Haemophilus, Pasteurella and Brucella.

20. The method of claim 8, wherein said ruminant is a member of a genus selected from the group consisting of Bos, Ovis, Capra, Lama, and Bison.

21. The method of claim 8, wherein said ruminant is a member of a genus Bos.

22. The method of claim 8, wherein said ruminant is a member of the species *Bos taurus*.

23. The method of claim 8, wherein the microbial infection is caused by one or more of Staphylococcus, Lactobacillus, Streptococcus, Sarcina, Escherichia, Enterobacter, Klebsiella, Pseudomonas, Acinelobacter, Proteus, Citrobacter, Nisseria, Bacillus, Bacteroides, Peptococcus, Clostridium, Salmonella, Shigella, Serratia, Haemophilus, Pasteurella and Brucella.

* * * * *